US007550291B2

(12) United States Patent
Belz et al.

(10) Patent No.: US 7,550,291 B2
(45) Date of Patent: Jun. 23, 2009

(54) VESSEL SYSTEM FOR THE TREATMENT AND/OR STORAGE OF LIQUIDS

(75) Inventors: Renato Belz, Emmenbrucke (CH); Armin Bucher, Steinhausen (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 186 days.

(21) Appl. No.: 10/657,308

(22) Filed: Sep. 8, 2003

(65) Prior Publication Data

US 2004/0234422 A1 Nov. 25, 2004

(30) Foreign Application Priority Data

Mar. 5, 2003 (DE) ............................ 203 03 538 U

(51) Int. Cl.
*C12N 1/00* (2006.01)

(52) U.S. Cl. ................................ 435/288.1; 435/288.3

(58) Field of Classification Search .............. 435/288.1, 435/288.3; *C12N 1/00*
See application file for complete search history.

(56) References Cited

U.S. PATENT DOCUMENTS 4,226,333 A * 10/1980 Percarpio .................... 215/247
5,683,659 A * 11/1997 Hovatter ..................... 422/102
5,720,406 A * 2/1998 Fassbind et al. ............ 220/23.4
6,776,964 B1 * 8/2004 Wijnschenk et al. .......... 422/99

FOREIGN PATENT DOCUMENTS

EP 836884 * 10/1997

* cited by examiner

*Primary Examiner*—David A Redding
(74) *Attorney, Agent, or Firm*—Charles M. Doyle

(57) ABSTRACT

Vessel systems for treating and/or storing liquids are provided. The vessel systems comprise a two-dimensional vessel arrangement with a plurality of vessels which are open at the top and which are interconnected to form a unit, and a two-dimensional closure arrangement which has an arrangement of closure elements corresponding to the vessel arrangement and by means of which the openings of the vessels can be closed. Each vessel of the vessel arrangement is connected to at least one other vessel of the vessel arrangement via a preferably flexible connecting member. Each of the closure elements is connected to at least one other closure element of the closure arrangement via a flexible connecting member which allows a change of the distance between the closure elements.

1 Claim, 5 Drawing Sheets

VESSEL SYSTEM FOR THE TREATMENT AND/OR STORAGE OF LIQUIDS

FIELD OF THE INVENTION

This application claims the benefit of priority under 35 U.S.C. §119 of German Utility Application No. 20303538.0, filed Mar. 5, 2003, the contents of which are hereby incorporated by reference.

The invention relates to a vessel system for the treatment and/or storage of liquids.

The invention also relates to a system for the storage and/or treatment of liquids with a vessel system according to the invention.

Particularly in the area of the treatment of nucleic acid samples, vessels are required which can be so held in the boreholes of a metal block incubator that there is an efficient heat transfer from the incubator to the liquids. For this purpose, thin-walled plastic vessels are normally used. When arrangements comprising a plurality of vessels are used, tilting may occur resulting in deterioration of the heat transfer. On the other hand, it is important that no individual vessels should be handled, in order to facilitate handling.

BACKGROUND OF THE INVENTION

From the document EP 0 642 828 A1, a vessel arrangement is known wherein the vessels are disposed along a circle and are interconnected via flexible connecting webs so that it is possible to press the vessels into the boreholes of an incubator even if the vessel position does not correspond completely to the positions of the boreholes in the incubator, as a result of production or temperature conditions. The number of vessels that can be flexibly connected in this way is limited, however, and any increase in the number of vessels results in a considerable increase in the space requirements.

A two-dimensional arrangement of vessels is known from EP 0 836 884 A2.

Particularly for the performance of polymerase chain reactions, and also for other incubation and thermocycling processes, in order to avoid contamination it is important that the vessels should be closed. In this connection it has been found difficult to produce a two-dimensional lid arrangement which would function approximately like the lid arrangement shown in document EP 0 642 828 A1.

The document WO 01/17682 A1 already discloses a two-dimensional arrangement of closure elements in the form of a continuous mat. However, it has been found disadvantageous for the vessel arrangement according to the invention if the closure elements are connected via a flexible mat. The main reason for this is that the flexibility between two adjacent closures is not sufficient to enable individual vessels to be closed separately.

SUMMARY OF THE INVENTION

The aim of the invention, therefore, is to provide a vessel system of the type described hereinbefore, which can be made with minimum cost and which does not have the disadvantages of known vessel systems or their closures.

According to a first aspect of the invention, this problem is solved with a vessel system which comprises (a) a two-dimensional vessel arrangement including a plurality of vessels which are open at the top and which are interconnected to form a unit, wherein each vessel of said vessel arrangement is connected to at least one other vessel of said vessel arrangement via a flexible connecting member, and (b) a two-dimensional closure arrangement which has an arrangement of closure elements corresponding to the vessel arrangement and by means of which the openings of the vessels can be closed, wherein each of the closure elements is connected to at least one other closure element of the closure arrangement via a flexible connecting member which allows a change of the distance between the closure elements.

The arrangement of the vessels is preferably square.

In a preferred embodiment of the vessel arrangement, the connecting member comprises a cross part between two closure elements, said cross part extending transversely of the connecting line between the closure elements and allowing changes in the distance between the closure elements.

In a preferred embodiment of the closure elements, the closure elements have a cylindrical recess open at the top, into which recess a pin can be pressed for closure purposes.

According to a second aspect of the invention, the above problem is solved with a system according to the invention for storing and/or treating of liquids comprising a vessel system wherein the closure elements have a cylindrical recess which is open at the top and in which a pin can be pressed for closure purposes, and wherein said closure device has a handle and a pin for introduction into the cylindrical recess in order to press the closure elements into the vessel openings.

According to a third aspect of the invention the vessel system according to the invention is used for performing temperature cycles.

The main advantage of the invention is that the vessel arrangement according to the invention and the closure arrangement are adapted to compact construction and yet relatively large numbers of vessels, and can be made at low cost. The vessel arrangement and closure arrangement according to the invention are therefore suitable for use as disposables. The flexible connections between the closure elements also enable convenient and safe handling, adjacent vessels being closable individually each with its closure without difficulty.

BRIEF DESCRIPTION OF THE DRAWINGS

The subject invention will now be described in terms of its preferred embodiments with reference to the accompanying drawings. These embodiments are set forth to aid the understanding of the invention, but are not to be construed as limiting.

REFERENCE NUMERALS IN DRAWINGS

Figure 1:
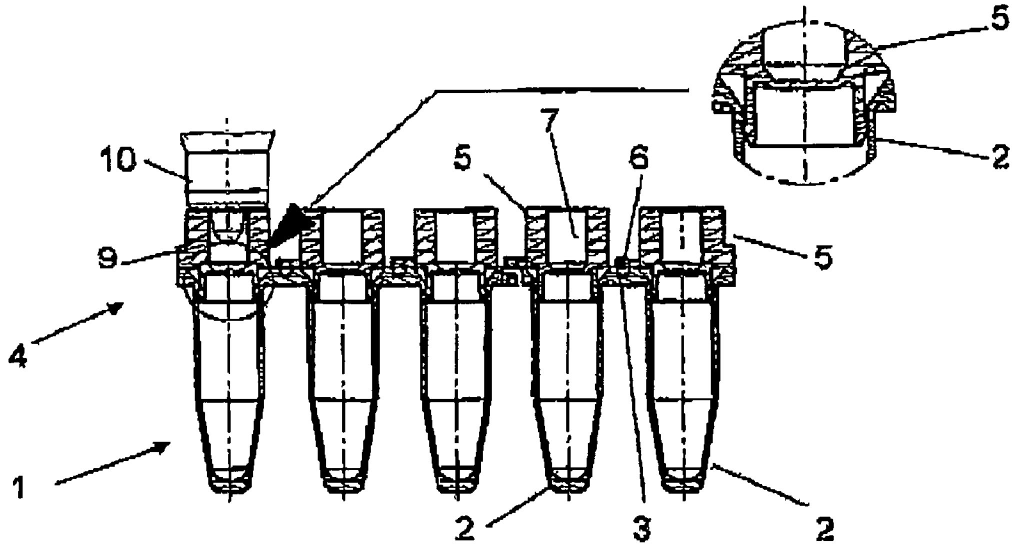
FIG. 1 shows a cross-sectional view of a vessel arrangement 1 and a closure arrangement 4 of vessel system according to the invention.

1. Vessel arrangement
2. Vessels
3. Connecting member
4. Closure arrangement
5. Closure element
6. Connecting element
7. Cylindrical recess
8. Cross part of 6
9. Pin of closure device
10. Handle of closure device
11. carrier element
12. barcode
13. connecting element
14. connecting element

DETAILED DESCRIPTION OF PREFERRED EMBODIMENTS

EXAMPLES

Example 1

Example of a Vessel System According to the Invention

The vessel system according to the invention as shown in FIG. 1 comprises a two-dimensional vessel arrangement 1 with a plurality of vessels 2 which are open at the top and which are interconnected to form a unit, and a two-dimensional closure arrangement 4, which has an arrangement of closure elements 5 corresponding to the vessel arrangement 1 to enable the openings of the vessel 2 to be closed.

In its middle position the vessel arrangement 1 does not have a vessel 2. The place in that position is used for automated handling of the vessel arrangement 1.

In its middle position the closure arrangement 4 has no closure element 5. The place in that position is used for automated handling of the closure arrangement 4.

Figure 3:
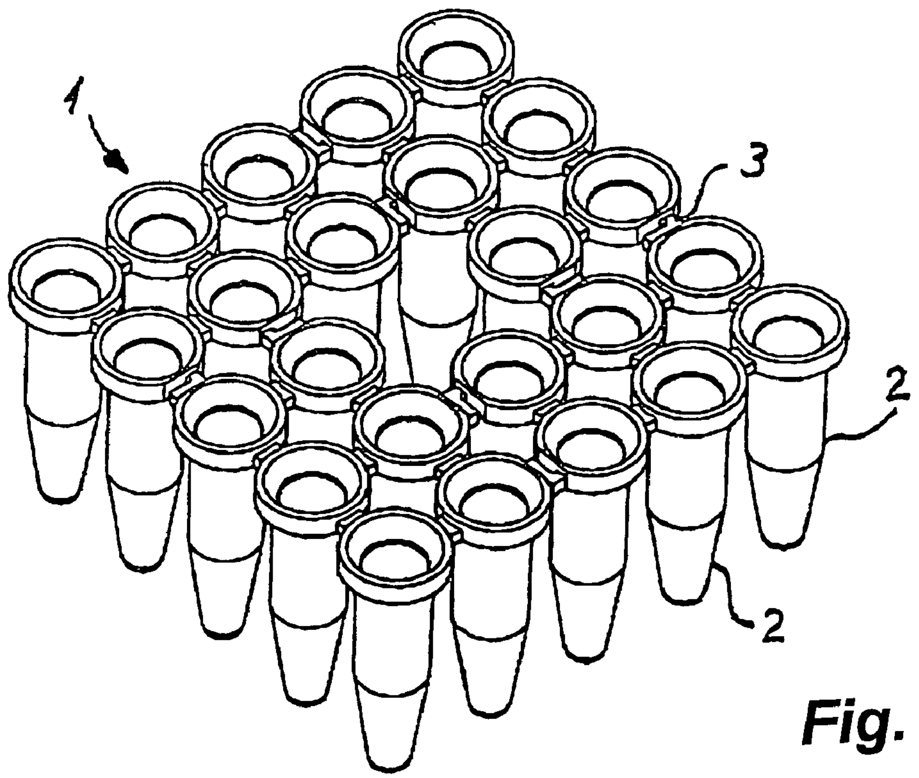
FIG. 3 and FIG. 4 are axonometric representations of the vessel arrangement and the closure arrangement shown in FIG. 1.

As shown in FIGS. 1 and 3, each vessel 2 of the vessel arrangement 1 is connected to at least one other vessel 2 of the arrangement 1 via a preferably flexible connecting member 3.

As shown in FIG. 3, the vessel arrangement 1 of vessels 2 is preferably square. As shown in FIG. 3, the vessels 2 are disposed, for example, in the form of a matrix.

Figure 2:
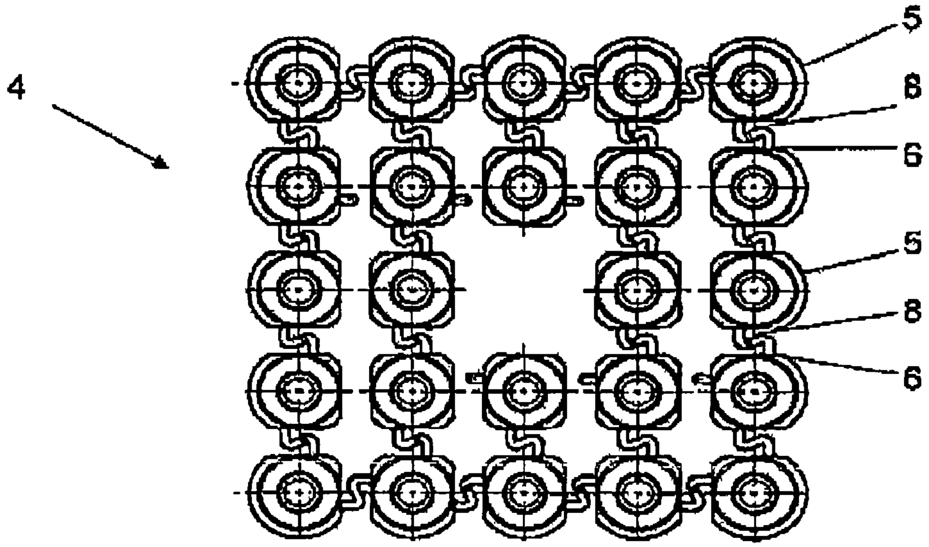
FIG. 2 shows a top view of the closure arrangement 4 of the vessel system shown in FIG. 1.
Figure 4:
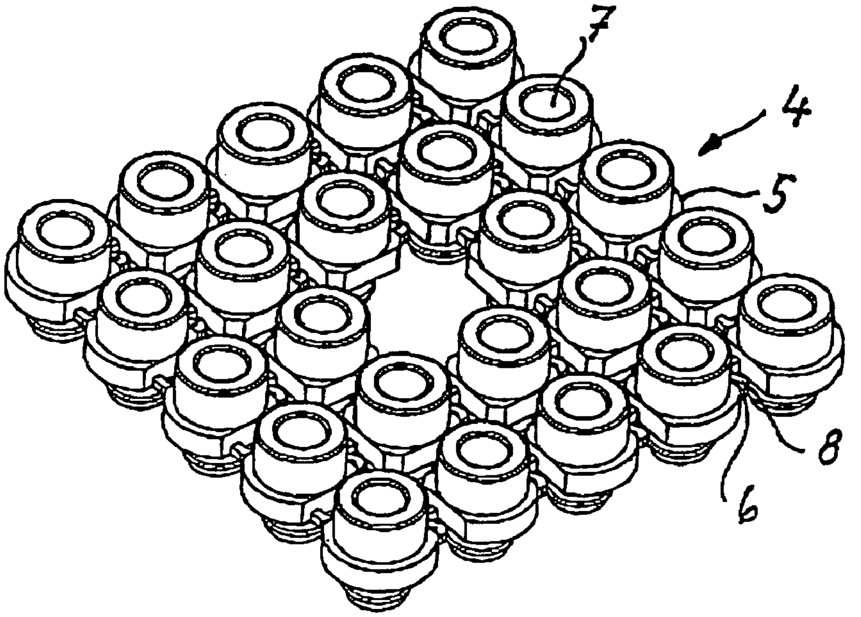
Figure 5:
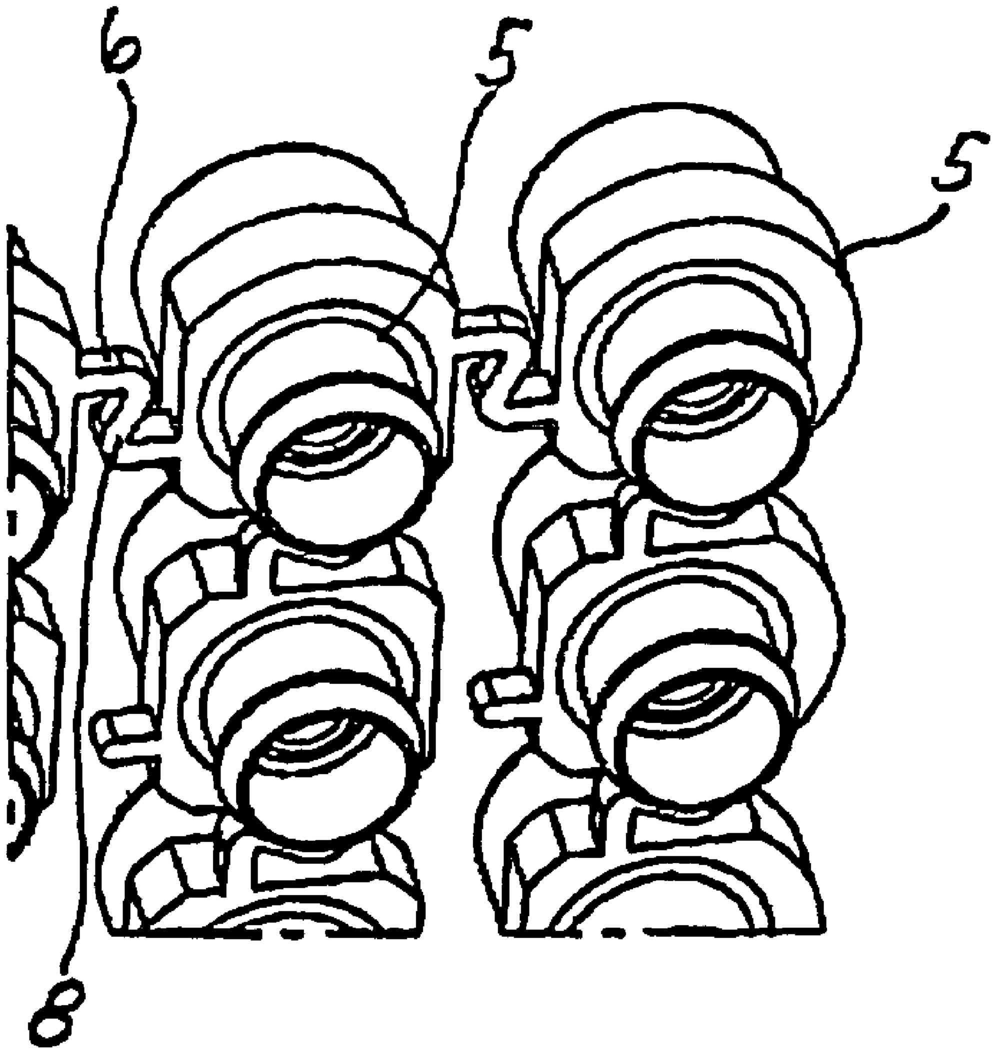
FIG. 5 shows a detail of the closure arrangement shown in FIG. 4.

As shown in FIGS. 2, 4 and 5, each of the closure elements 5 is connected to at least one other closure element 5 of the vessel arrangement 1 via a flexible connecting member 6 which acts as a spring element and enables the distance between the closure elements 5 to be varied.

In the preferred embodiment, the connecting member 6 between two closure elements 5 has a cross part 8 which extends transversely of the connecting line between the closure elements 5 and enables the distance between the closure elements 5 to be varied.

As will be apparent from FIGS. 2 and 5, each of the connecting members 6 preferably has a Z structure, the connecting members having a cross part 8 which extends transversely of the connecting line between the vessels 2. If the distance between two connected vessels 2 has to be changed for fitting in an incubator, it is a simple matter because of the cross part 8.

The closure arrangement 4 according to the invention enables the user to close each of the vessels 2 individually in order to ensure that none of the vessels 2 remains unclosed. In this connection it is important that a connecting member should hold the closure only in one direction in space and not in four directions in space, as is the case in the closure mat in WO 01/17682 A1.

As shown in FIGS. 1 and 4, each closure element has a cylindrical recess 7 open at the top into which a pin 9 shown in FIG. 1 can be pressed for closure purposes.

The vessels 2 of the vessel arrangement 1 and closure elements 5 of the closure arrangement 4 are preferably made from a material suitable for the performance of PCR processes, for example polypropylene.

Both the vessel arrangement 1 and the closure arrangement 4 can be made inexpensively with a one-component tool by an injection molding process.

Figure 6:
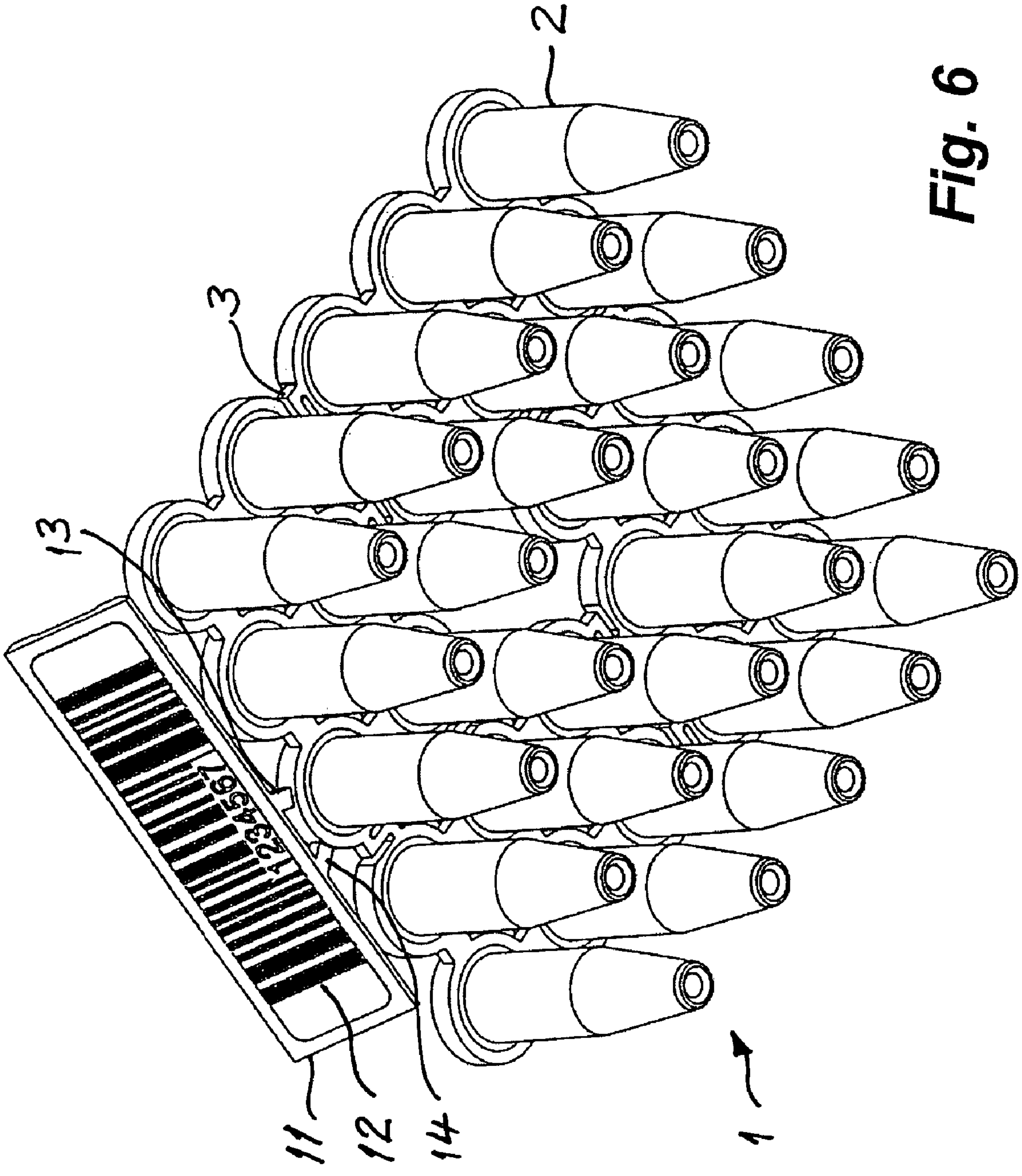
FIG. 6 shows a first perspective view of an embodiment of a vessel arrangement 1 including a barcode carrier 11 connected to the vessel arrangement 1.
Figure 7:
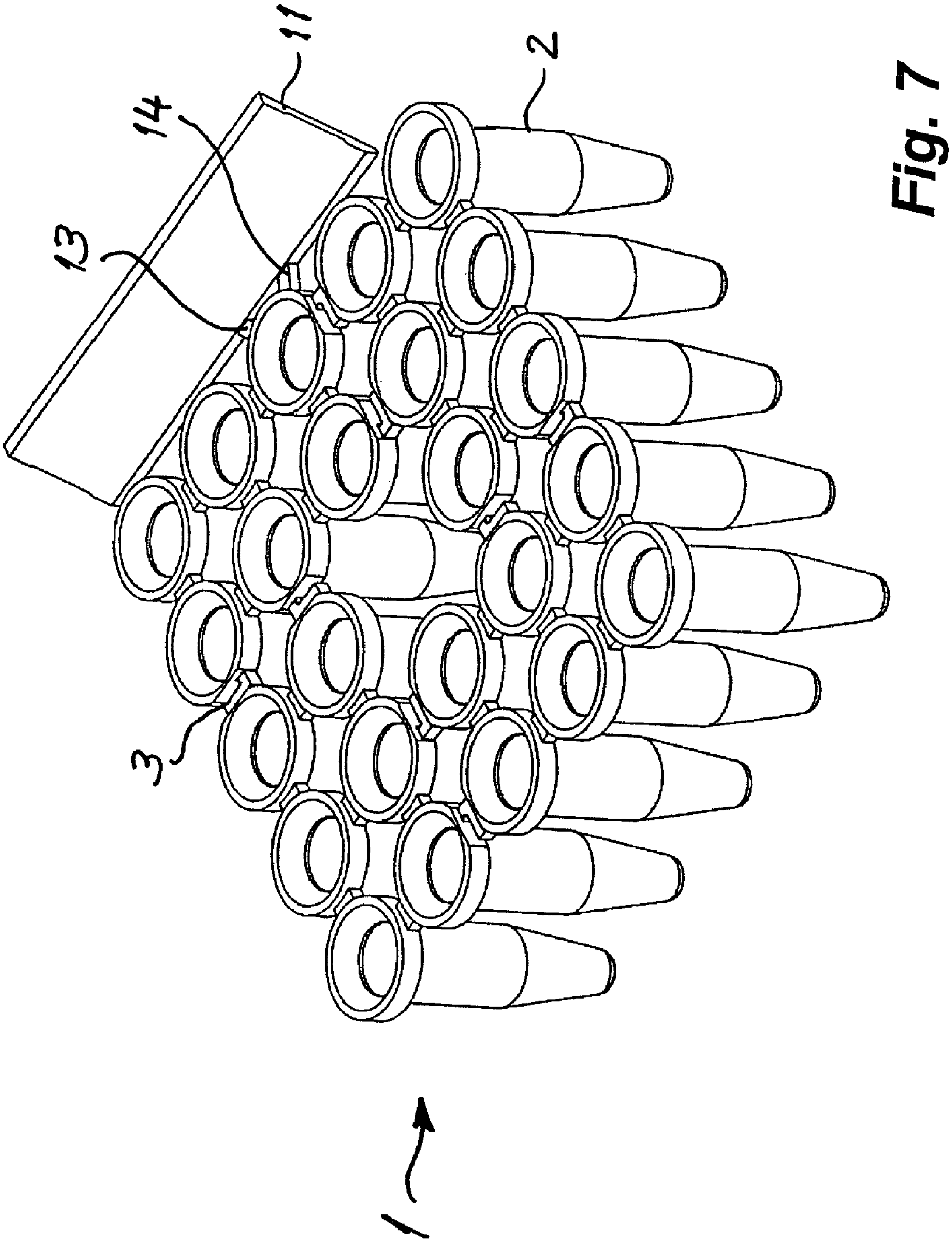
FIG. 7 shows a second perspective view of the embodiment of a vessel arrangement 1 shown in FIG. 6.

FIGS. 6 and 7 show a preferred embodiment of the above-described vessel arrangement 1. This preferred embodiment includes a barcode carrier 11 for carrying a barcode label 12. Connecting elements 13 and 14 connect barcode carrier 11 to one of the vessels 2 and thereby to vessel arrangement 1.

Example 2

Example of a System According to the Invention

A system for the storage and/or treatment of liquids according to the invention comprises:

- a vessel system 1 of the type described above wherein each closure element has a cylindrical recess 7 open at the top, into which a pin 9 shown in FIG. 1, can be inserted to dose a vessel 2 with a closure element 5, and
- a closure device which comprises a handle 10 and a pin 9 for introduction into the cylindrical recess 7 in order to press the closure elements into the vessel openings.

The closure device used preferably has a handle with a pin 9 fixed on the front of the handle 10.

Example 3

Example of Use According to the Invention of the Vessel System or System Described Above A vessel system 1 or a system of the above-described type is usable particularly for performing temperature cycles such as those, for example, carried out in the area of treating nucleic acid samples.

Modifications and variations of the above-described exemplified embodiments will be recognizable to the skilled man. The above description of one exemplified embodiment is therefore intended to describe one preferred embodiment. Details of the described vessel system or the described system for storing and/or treating liquids can therefore be changed without departing from the spirit or scope of the following claims.

What is claimed is:

1. A vessel system for treating and/or storing liquids comprising (a) a matrix array of vessels arranged in a square format, wherein the vessels are open at the top and are interconnected to form a unit and each vessel of said array of vessels is connected to at least one other vessel of said array via a flexible connecting member;

(b) a matrix array of closure elements corresponding to the matrix array of vessels, wherein the openings of the vessels can be closed with the closure elements and each of the closure elements is connected to at least one other closure element of the array of closures via a flexible connection member that allows a change in the distance between the closure elements, said flexible connecting member comprising a cross part between two closure elements, said cross part extending transversely to the connecting line between the closure elements, said closure elements having a cylindrical recess open at the top into which a pin can be pressed to close the openings of the vessels, and (c) a closure device that comprises a handle and a pin for introduction into the cylindrical recess in order to press the closure elements into the vessel openings.

* * * * *